(12) United States Patent
Bullen

(10) Patent No.: US 6,921,896 B2
(45) Date of Patent: Jul. 26, 2005

(54) AUTOMATIC BACKSCATTER GAUGE

(75) Inventor: George Nicholas Bullen, Oxnard, CA (US)

(73) Assignee: Northrop Grumman Corporation, Los Angeles, CA (US)

( * ) Notice: Subject to any disclaimer, the term of this patent is extended or adjusted under 35 U.S.C. 154(b) by 133 days.

(21) Appl. No.: 10/279,274

(22) Filed: Oct. 24, 2002

(65) Prior Publication Data
US 2004/0079882 A1 Apr. 29, 2004

(51) Int. Cl.⁷ ............................................... G01N 23/00
(52) U.S. Cl. ...................................................... 250/308
(58) Field of Search ............................... 250/308, 393, 250/336.1, 358.1

(56) References Cited

U.S. PATENT DOCUMENTS

| | | | |
|---|---|---|---|
| 4,383,327 A | | 5/1983 | Kruger |
| 4,612,660 A | | 9/1986 | Huang |
| 4,825,454 A | | 4/1989 | Annis et al. |
| 5,068,883 A | * | 11/1991 | DeHaan et al. ............... 378/86 |
| 5,294,803 A | * | 3/1994 | Pahr ....................... 250/559.36 |
| 5,351,203 A | * | 9/1994 | Hoffman et al. ............ 701/172 |
| 5,590,060 A | * | 12/1996 | Granville et al. ........... 702/155 |
| 5,763,886 A | * | 6/1998 | Schulte .................... 250/358.1 |
| 5,798,925 A | | 8/1998 | Poling |
| 5,805,662 A | | 9/1998 | Kurbatov et al. |
| 5,821,862 A | | 10/1998 | MacKenzie |
| 5,871,391 A | * | 2/1999 | Pryor ............................ 451/9 |
| 6,049,282 A | | 4/2000 | MacKenzie |
| 6,081,580 A | | 6/2000 | Grodzins et al. |
| 6,282,260 B1 | | 8/2001 | Grodzins |
| 6,421,418 B1 | * | 7/2002 | Schulte ........................ 378/89 |

FOREIGN PATENT DOCUMENTS

WO     WO 97/01089     1/1997

* cited by examiner

Primary Examiner—David Porta
Assistant Examiner—Marcus Taningco
(74) Attorney, Agent, or Firm—Stetina Brunda Garred & Brucker

(57) ABSTRACT

In an embodiment of the present invention, the same provides an edge sensor capable of locating an edge under a substrate. The edge sensor comprises a radiation source, a scanner, a microprocessor, and an indicator. The radiation source emits photons that are scattered back to the direction of the radiation source. The scanner measures the count rate or the amount of radiation back scattered by the substrate along a line on the substrate. After a series of count rates have been measured at various points along a line on the substrate that data is received and the microprocessor calculates a response function centroid which is the position of the edge. The indicator indicates the edge position.

24 Claims, 4 Drawing Sheets

AUTOMATIC BACKSCATTER GAUGE

CROSS-REFERENCE TO RELATED APPLICATIONS (Not Applicable)

STATEMENT RE: FEDERALLY SPONSORED RESEARCH/DEVELOPMENT (Not Applicable)

1. Field of the Invention

The present invention relates generally to a nondestructive inspection device. In particular, the inspection device detects and locates the exact position of changes in substrate thicknesses.

2. Background of the Invention

In manufacturing, it is sometimes necessary to locate an edge that is not visible to a drill operator. For example, if a plate joined two skins of a plane together with rivets, then the plate would have an edge located a distance from the edge of the skin. Additionally, if the design called for a hole to penetrate through the skin but not the plate then the drill operator must be able to locate the plate edge so as to avoid damage to the plate by the drill bit. If the plate was visible to the drill operator then the drilling operation would be a simple operation. However, when the drill must enter on the blind side of the skin, then there must be a method or tool to allow a drill operator to drill close to the plate edge yet avoid damage to the plate edge. The blind side of the skin being the side where the plate edge is not visible.

A reason that avoiding damage to the plate is important is that if the plate is subject to high stress fatigue then any plate damage may cause stress concentration in the plate that may lead to failure thereby disjoining the two skins. Additionally, if the drill bit touched the plate edge then the drill bit would tend to drift. As a result, the drilled hole would not be located in the proper location. Furthermore, the hole would not be perpendicular to the surface of the skin. Additionally, the drilled hole would not be round compared to a hole that did not touch the plate edge.

BRIEF SUMMARY OF THE INVENTION

In an embodiment of the present invention, the same provides an edge sensor for identifying a position of an edge on a substrate. The edge sensor includes a radiation source, a scanner, a microprocessor, and an indicator. The radiation source is capable of emitting radiation backscatterable by the substrate. The radiation is further collimated by a collimator. The radiation source may be contained within a stainless steel cylinder. The radiation source emits radiation at levels of approximately 0.8 microSievert/hr or 0.08 millirem/hr at 12 from the gauge tip for 241 AM, and 0.5 mSv/hr or 0.05 mrem/hr for 57 Co.

The scanner is attached to the radiation source and detects a count rate from the radiation backscattered by the substrate. In particular, the scanner is a cesium iodide crystal which has a thin annular shape. The scanner is attached to the radiation source such that it surrounds the collimator. The scanner outputs the count rate. A charge sensitive amplifier may be attached to the scanner with a shielded cable.

The position sensor is capable of locating a position of the backscattered radiation on the substrate.

The microprocessor is in electrical communication with the scanner and position sensor which receives the count rate and the positional data therefrom, then calculates the edge position.

The indicator receives and indicates the calculated edge position. The indicator may be a monitor which depicts the edge position as a response function centroid. Alternatively, the indicator may be a light emitting diode which is turned on or off when a locating wand is moved across the edge.

In another embodiment of the present invention, the same provides an edge sensing CNC machine which machines parts. The machine comprises a CNC machine and an edge sensor. The edge sensor identifies a position of an edge on a substrate In relation to the edge sensor, the edge sensor comprises a radiation source, a scanner, a position sensor, and a microprocessor. The radiation source is capable of emitting radiation backscatterable by the part. The scanner is attached to the radiation source for detecting a count rate from the radiation backscattered by the part. The position sensor is capable of locating a position of the backscattered radiation on the part. The microprocessor in electrical communication with the scanner and position sensor which receives the count rate and the positional data therefrom, then calculates the edge position.

In another embodiment of the present invention, the same provides for a method of locating an edge under a substrate. The steps of the method comprises an emitting step, a detecting step, a determining step, and a indicating step. The emitting step emits a beam of backscatterable radiation onto the substrate. The beam shape may be collimated. Additionally, a collimator may collimate the beam.

The detecting step detects the radiation backscattered from the substrate before the edge, as the beam crosses the edge defining a response function, and after the edge. The detecting step may be accomplished with a scanner. The scanner may be a cesium iodide crystal having a thin annular shape. Lastly, the scanner may be positioned so as to surround the collimator.

The determining step determines the response function centroid from the detected radiation backscattered from the substrate.

The indicating step indicates the position of the edge.

BRIEF DESCRIPTION OF THE DRAWINGS

These as well as other features of the present invention will become more apparent upon reference to the drawings wherein.

DETAILED DESCRIPTION OF THE INVENTION

An example of the present invention for purpose of illustrating the preferred embodiments only, and not for purposes of limiting the same is discussed. Additional modifications and improvements of the present invention may also be apparent to those of ordinary skill in the art. Thus, the particular combination of parts described and illustrated herein is intended to represent only certain embodiments of the present invention, and is not intended to serve as limitations of alternative devices within the spirit and scope of the invention.

Figure 1:
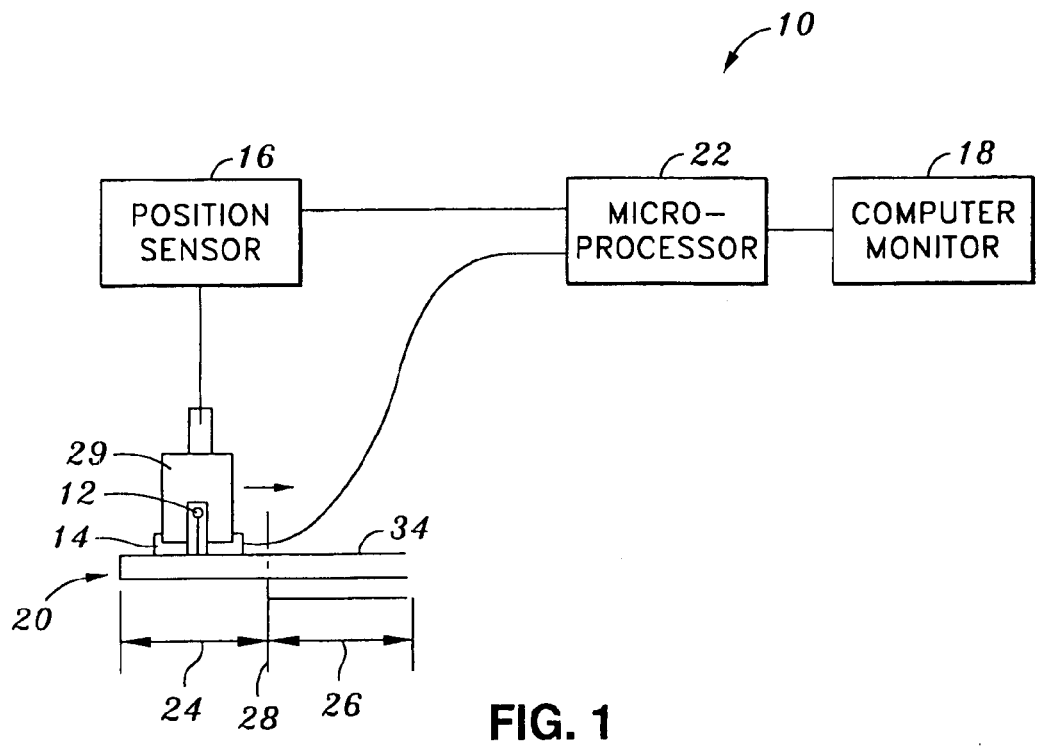
FIG. 1 depicts the edge sensor.

Referring to FIG. 1, the same depicts an edge sensor 10 which comprises a radiation source 12, a scanner 14, a position sensor 16, and an indicator 18.

In the general operation of the edge sensor 10, the radiation source 12 emits radiation onto a substrate 20 which reflects back or backscatters the radiation. In other words, at least a partial amount of radiation is not absorbed by the substrate 20 and did not penetrate through the substrate 20. The scanner 14 detects the count rate of the backscattered radiation and transmits the count rate to a microprocessor 22. Simultaneously, a position sensor 16 locates the center of the emitted radiation on the substrate 20. Both the count rate and its position are associated and relayed to a microprocessor 22. These steps are repeated along one dimension of the substrate 20 at small incremental distances at a selectable scan rate to obtain the edge position.

Figure 2:
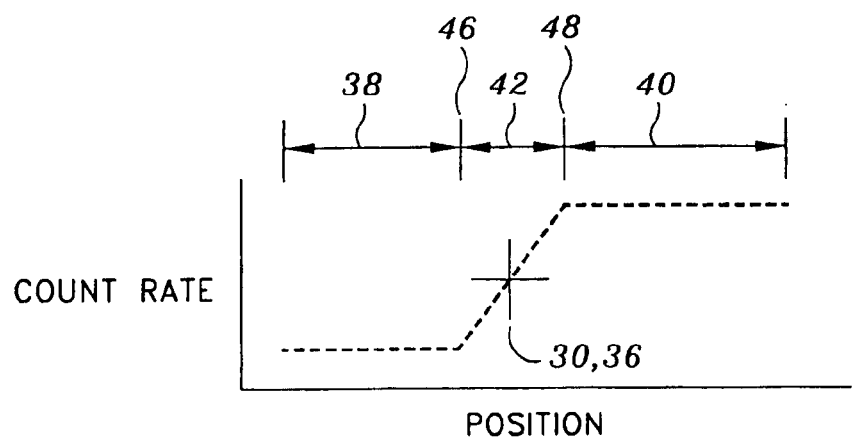
FIG. 2 graphs count rate in relation to position.

The count rates and corresponding count rate positions are collected in a microprocessor 22 that collects, analyzes and sends the data and/or calculated edge position to the indicator 18. The indicator 18 may be a monitor that displays a graph thereof, as shown in FIG. 2. For example, if the edge sensor 10, as shown in FIG. 1, scanned the substrate 20 from the substrate thin portion 24 to a substrate thick portion 26, then a graph similar to FIG. 2 would be displayed. When the edge sensor 10 scanned the substrate thin portion 24, the substrate thin portion 24 had less backscatter compared to the backscatter at the substrate thick portion 26. Additionally, the transition period as the edge sensor 10 scanned the edge 28 reveals a rising increase in backscatter, hereinafter response function 42. In some instances the increase is linear.

The microprocessor 22 further determines statistically similar count rates for the substrate thin and thick portion 24, 26. The microprocessor 22 averages the count rates then in relation to the response function determines the edge position. In particular, the count rates 38, 40 before and after the scanner passes an edge are averaged and the intersection of the averaged count rate and the response function 42 identifies the edge position, hereinafter centroid 36.

A discussion of the general component parts of the edge sensor 10 shall be discussed. The radiation source 12 emits photons which are not completely absorbed by the substrate 20 and does not completely penetrate the substrate 20. In effect, at least some of the photons are reflected away from the substrate 20 or backscattered by the substrate 20. In this regard, the level of photons reflected away from the substrate 20 or its count rate is a function of the substrate thickness, material type, and density.

The photons emitted by the radiation source 12 should at least reach the thick portion 26 of the substrate 20. In other words, at least some of the photons must pass through the thin portion 24 of the substrate 20. In this regard, the edge locating ability of the edge sensor 10 is not affected by the thickness of the thick portion 26 of the substrate 20 provided that the thin portion 24 of the substrate 20 does not exceed an effective penetration depth of the radiation source. In this manner, there will be a variation of count rates through a one dimensional cross section of the substrate 20 having various abrupt or gradual changes in thickness. For example, when the edge sensor 10 travels from a substrate thin portion 24 to a substrate thick portion 26, the backscatter count rate increases linearly because more of the photons are being reflected back.

An appropriate radiation source 12 maybe selected which is appropriate to the substrate thickness, material type, and density. By way of example and not limitation, the effective penetration depth of Americum-241 and Cobalt-57 are given. The effective penetration depth of Americum-241 which emits 60 keV gamma rays being 12 mm for Aluminum and 18 mm for composites. The effective penetration depth of Cobalt-57 which emits 122 keV gamma rays being 0.591 inch (15 mm) for Aluminum and 0.905 inch (23 mm) for composites.

The radiation source 12 does not require any calibration. It works strictly on a relative measurement. In this regard, the edge sensor 10 may be utilized on an aluminum substrate then immediately utilized on a composite substrate without any need to re-adjust or calibrate the radiation source 12.

The radiation source 12 does require replacement. In particular, the recommended lifetime of Americum-241 is 15 years. During this time, there will be no noticeable change in the source strength. For Cobalt-57, the source strength diminishes over a much shorter time period. In particular, the strength will be reduced by half its original strength in approximately nine months. As a result, the radiation source 12 must be replaced every eight to ten months. To extend the useful life of the radiation source 12, the scan rate of the edge sensor 10 may be reduced to approximately one inch per minute without any loss in edge sensing capability (i.e., effective penetration depth and accuracy) from a normal scan rate being 2.5 inches per minute.

The accuracy of the edge sensor 10 in its ability to detect the location of an edge 28 is dependent on the scan rate. In an embodiment of the present invention, the ideal scan rate is about 2.5 inches per minute, as discussed above. When the scan rate is reduced, the substrate 20 will tend to absorb and reflect back the absorbed radiation. In this regard, the scanner 14 is unable to determine whether the detected radiation is from the absorbed radiation or the backscattered radiation. This reduces the accuracy of the edge sensor 10. A microprocessor 22 could be utilized to calculate the amount of radiation being scanned due to the absorbed radiation to mitigate the effects therefrom. As such, the interference from the absorbed radiation may be mitigated to reduce its effect on the accuracy of the edge sensor 10. The microprocessor 22 may calculate the amount of backscatter due to the absorbed radiation as a function of prior historical data of the current scan or prior scan(s).

When the scan rate is increased, the substrate 20 absorbs less radiation thereby decreasing the effect of the absorbed radiation. However, an increase in scan rate correspondingly reduces the amount of data points thereby reducing the accuracy of the edge sensor 10. In relation to the scan rate, an optimal scan rate balances the two factors, namely, absorption and data points.

The radiation source 12 may be contained in a container 29 with an aperture which emits the photons directed toward the substrate 20. The radiation source 12 may also be placed within a collimator which produces a focused collimated beam of photons. Preferably, the photon beam shape is a thin column. In general, the accuracy of the edge sensor 10 is dependent on the radiation beam configuration and the level of the reflected photons.

In relation to the beam configuration, the accuracy of the edge sensor 10 increases as the beam is more focused. The beam although emitted through a collimator has a diameter. In this regard, the response function 42 is a function of the beam diameter. The response function 42 has four characteristics, namely, a starting point 46, terminating point

48, a slope, and a centroid 36. The starting point 46 signifies that the outer diameter of the beam has begun to detect the edge 28. The terminating point 48 signifies that the outer diameter of the beam has finished detecting the edge 28. The slope represents the increase or decrease of backscattered radiation depending on the direction of the scan. The centroid 36 represents the edge position 30. As the beam becomes more focused, the slope of the response function 42 approaches infinity. The starting point 46, terminating point 48, and the centroid 36 may be used to locate the edge 28. The method of calculating the centroid 36 is discussed in detail below.

Additionally, the accuracy of the edge sensor 10 increases as more radiation is reflected back to the scanner 14 by the substrate 20 as a function of the substrate thickness. The amount of radiation reflected back to the scanner 14 may be increased by utilizing a radiation source which emits more radiation.

The radiation emitted from Americum-241 or Cobalt-57 contained within a stainless steel container 29 is at a sufficiently low level that current occupational standards do not require exclusion zones or radiation badges. The container 29 has an aperture from which radiation is emitted onto the substrate 20. The dose rate of the emitted radiation from the aperture is very low. The dose rate is approximately 0.8 microSievert/hr or 0.08 millirem/hr at twelve inches from the tip for Americum-241 and 0.5 mrem/hr for Cobalt-57. Whenever the end cap covering the aperture is in place, there is no radiation emitted from the container 29. It is recommended that the end cap be placed on the aperture whenever the edge sensor 10 is not in use.

The scanner 14 detects the count rate of radiation backscattered from the substrate 20. In other words, the scanner 14 detects the reflected photons from the substrate 20. In particular, by way of example and not limitation, the scanner 14 may be a cesium iodide crystal. Preferably, the cyrstal has a thin annular shape which surrounds the collimator or container 29. The thickness of the crystal being less than about 0.100 inches. As the crystal thickness increases, the accuracy of the edge sensor is reduced due to the increase in distortion of the crystal.

The crystal is attached to a Lucite light guide. The Lucite light guide is connected to a photomultiplier tube which amplifies the electrical signal produced by the crystal. Preferably, the photomultiplier is physically located close to the crystal. More preferably, the photomultiplier is physically mounted on the crystal. The physical closeness of the photomultiplier with the crystal mitigates against any electrical noise from the system that may affect the accuracy of the edge sensor. The output of the photomultiplier tube is connected to a charge sensitive amplifier and a voltage comparator.

The charge sensitive amplifier magnifies the count rate to a significant level. In particular, as discussed above, the radiation source 12 emits a negligible amount of photons or radiation and the accuracy of the sensor 10 is dependent on the count rate level. In an embodiment of the present invention, the scanner 14 is unable to independently receive a significant radiation count rate level. As such, the scanner 14 is coupled with a charge sensitive amplifier which magnifies the count rate readings to a noticeable level. Although the charge sensitive amplifier is an off-the-shelf component, through tests it has been determined that amplification of the signal with a charge sensitive amplifier is capable of providing an accurate edge position 30.

The position sensor 16 relates a count rate position to the count rate along one line of the substrate 20. The length of the scan must be long enough to obtain a statistically significant difference between the measured count rate of the substrate thin and thick portions 24, 26. A statistically significant count rate is approximately 30 readings. A typical scan rate being approximately 2.5 inches per min (63.5 mm/min). The scan rate may be slowed to approximately one inch per minute (25 mm/min.) to account for a reduction of radiation source strength over the life of the radiation source 12. The purpose of reducing the scan rate is to maintain the edge position accuracy when the radiation source 12 loses its strength.

The edge sensor 10 may make multiple parallel passes across the substrate 20 offset from one another. The offset preferably being approximately a quarter of an inch. In this regard, a two dimensional topography of the substrate identifying the edge is obtained. The centerline of the line may follow the estimated edge position so that the estimated edge position fluctuates about the median of the line length.

The position sensor 16 may be an electronic measuring wheel fixedly attached to the scanner 14 and radiation source 12. In this regard, as the edge sensor 10 moves along the substrate 24, 26, the wheel rotates proportionally to the distance traveled by the edge sensor 10. The wheel is calibrated to send out a signal to a microprocessor 22 at set intervals during its rotational movement. For example, it may send out sixty signals during one revolution. Since the circumference of the wheel is known, as long as each of the 60 signals are sent at equal intervals, the distance between each of the intervals are also known. In this regard, a count rate is associated with a numbered signal which is equivalent to a distance from a starting or reference point on the substrate 24, 26. The position of the sensed radiation must be calibrated in relation to the distance to the position sensor.

The position sensor 16 may be a computer numerically controlled machine (CNC machine). In this regard, the radiation source 12 and the scanner 14 may be fixedly attached to a drill chuck on the CNC machine. The portion of the substrate 20 responsible for the radiation backscattering maybe aligned with the centerline of the drill chuck. In this regard, the CNC machine may relay count rate positional data to the microprocessor 22.

The indicator 18 indicates the edge position to the drill operator. By way of example and not limitation, the indicator 18 may be a computer monitor or a red/green light. In relation to the red/green light, the count rate and position is relayed to a microprocessor which in turn determines the edge position. When the scanner crosses the edge, a green light will activate. When the scanner is not located at the edge, then a red light will be activated and the green light is deactivated.

Figure 3:
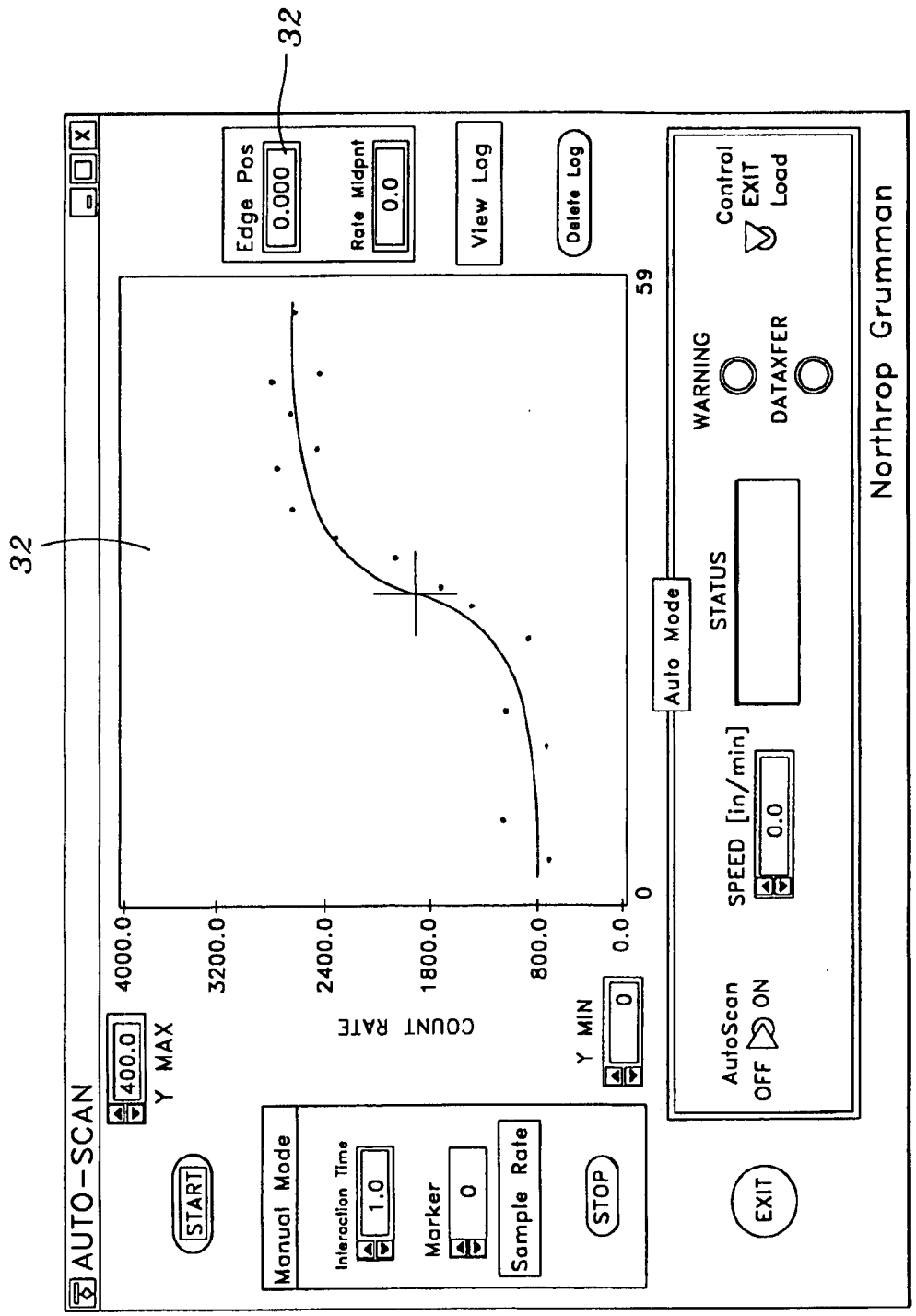
FIG. 3 is an indicator as embodied in the form of a computer monitor.

In relation to the computer monitor, an edge position 30 and a strip chart 32 is displayed on the monitor, as shown in FIG. 3. The edge position 30 indicates the distance of the detected edge from a reference point. The reference point being where the scanner 14 began to scan a substrate blind surface 34. In this regard, the user may use the edge position to identify a drill position that will not interfere with a drilled hole.

The strip chart 32 allows a visual inspection of the received data (i.e., count rate and position data) to make a visual validation of the edge position 30 displayed on the computer monitor. In this regard, the strip chart 32 allows a visual inspection to ensure that all the data appears to conform to the expected graphical form. For example, if all data points appear to form a smooth curve except for one data point, then the strip chart 32 indicates that all the data points may not have been reliably obtained and that the substrate 20 should be re-scanned.

In operating the edge sensor 10, the radiation source 12 emits photons that are backscattered by the substrate 20 and is received by a scanner 14. The count rate or the amount of photons received by the scanner 14 is associated with a position on a substrate blind surface 34. A series of count rates are measured along one line along the substrate blind surface 34. As the edge sensor 10 travels across the substrate 20, a statistically equivalent count rate will be received for a substrate 20 of common thickness. As the edge sensor 10 encounters an edge 28, the change in count rate varies, as shown in FIG. 2 which shows the response function 42 to a scan across a sharp edge 28. The centroid 36 of the response function 42 precisely determines the edge position 30 as shown by the cross hairs in FIG. 2.

During the operation of the edge sensor 10, the first statistically equivalent count rate is averaged with the second statistically equivalent count rate. The first count rate 38 is determined when the scanner 14 has not encountered the edge 28. The second count rate 40 is determined when the scanner 14 has completely passed the edge 28. As such, the first and second count rate should be statistically different. In addition to the count rates being statistically different, a response function 42 is also determined. In this regard, the first and second count rates 38, 40 are averaged and the intersection between the averaged count rates and the response function 42 defines the edge position 30 and centroid 36.

Figure 4:
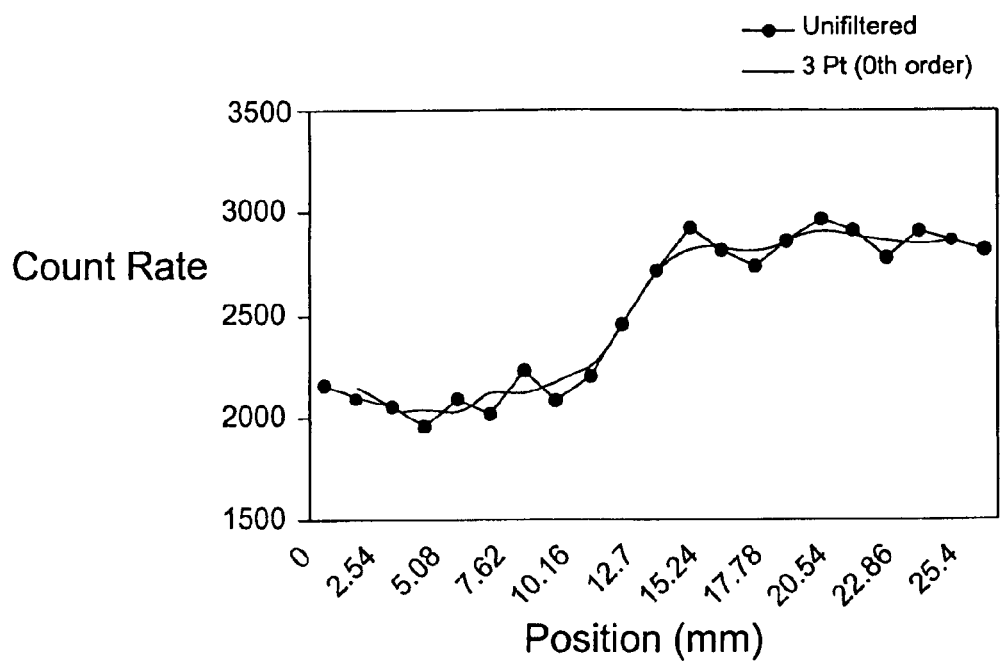
FIG. 4 is a typical scan measurement shown by the data points where the smooth curve is the result of applying a 3-pt, zeroeth order filter to the data.

The graph of count rates as a function of edge position 30 varies along the length of the scan. As such, data filtering or smoothing techniques can be used to reduce this scatter. A 3-point ($0^{th}$ order) and a 5-point ($2^{nd}$ order) filter may be used for the scanned data. The results of the 3-point and 5 point smoothing techniques are similar as shown in FIG. 4.

The accuracy of the edge position may be increased in the following methods. First, the accuracy of the edge sensor 10 in locating an edge 28 is increased as a function of scan rate. In particular, as the scan rate is reduced the edge 28 is located more accurately. Second, the edge sensor 10 may scan a substrate 20 along a line until an edge 28 is detected. Upon detection, multiple scans are made over that edge 28. After each scan, the length of the scan line is truncated at both ends until the line is truncated to an exact point thereby locating the edge 28. In this regard, time is reduced because the edge sensor 10 is not required to travel the complete original distance of the scan. Additionally, less radiation is used to locate the exact location of the edge 28 thereby mitigating against the negative effects of radiation absorption by the substrate 20.

Third, the position sensor 16 is calibrated to determine the center of the sensed backscattered radiation. In particular, the position sensor 16 and the sensed backscattered radiation are calibrated in relation to each other. Fourth, as discussed above, radiation absorbed by the substrate 20 reduces the accuracy of the edge sensor 10. However, this accuracy reduction may be mitigated by taking multiple scans along two close parallel lines which scan essentially the same edge. In particular, the edge sensor will scan a first line which passes over the edge. Thereafter, the edge sensor will scan a second line parallel to the first line but offset therefrom. The offset distance being sufficient such that the radiation absorbed by the substrate due to the scanning of the first line only negligibly interferes with the scanning of the second line. The first and second line may then be re-scanned. This method allows the radiation absorbed by the first scan to dissipate such that the second iteration of scanning is not affected by any absorbed radiation by the substrate due to the first iteration. The above described methods may be implemented individually or in combination with each other.

Various tests were conducted to evaluate the applicability of the edge sensor. A discussion of those tests will be discussed.

Figure 6:
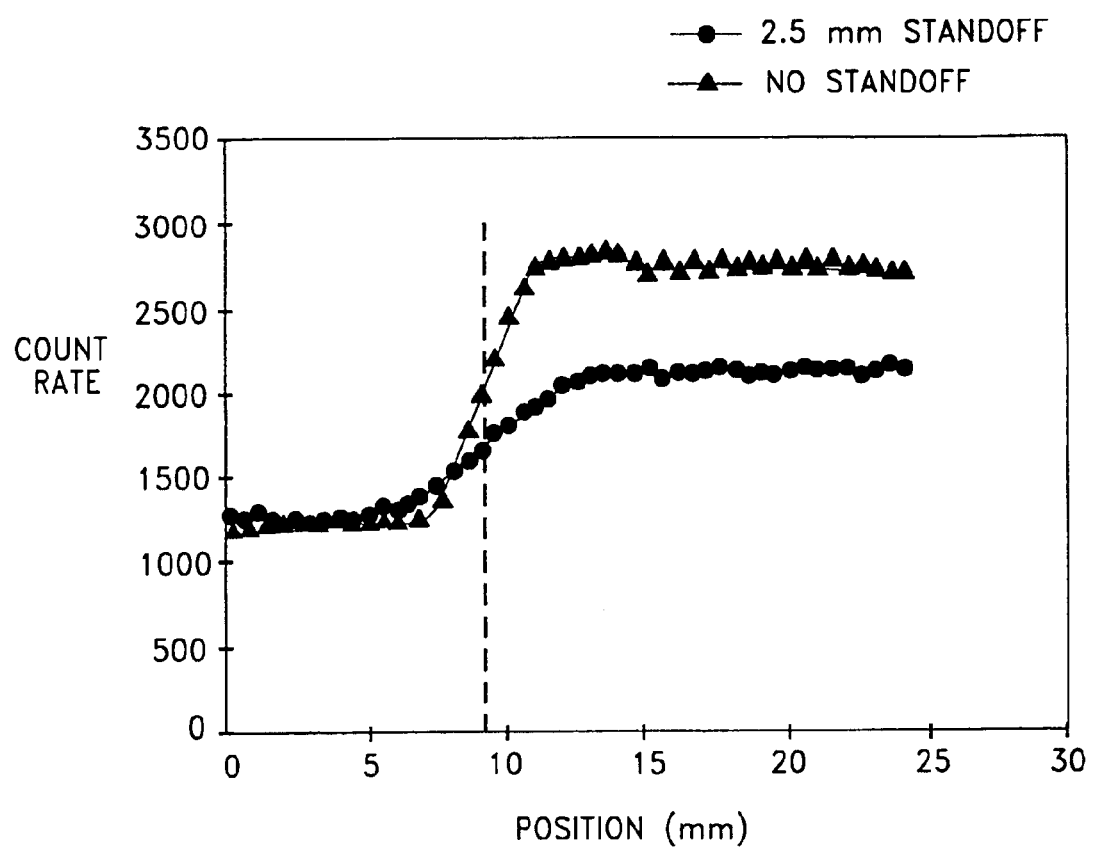
FIG. 6 is edge position measurements with the container aperture in contact with the substrate blind surface and standing off from the substrate surface.

A first test measured the ability of the edge sensor 10 to sense an edge 28 when the container aperture had a stand off from the surface. In other words, when the scanner 14 and radiation source 12 do not contact the substrate surface. FIG. 6, in particular, shows the results of two scans over a substrate 20 of a 0.122 inch (3.1 mm) thick aluminum substrate and a 0.256 inch (6.5 mm) thick aluminum flange under the substrate 20. For the first scan the container aperture is in contact with the substrate surface (i.e., no standoff) and for the second scan the container aperture stands off the substrate surface 0.374 inches (9.5 mm). In comparing the two scans, the count rate differential is decreased by 25%. In other words, the response function slope is reduced. However, the count rate differential between the thin and thick sections is more than adequate to make a precise determination of edge position for both scans.

Figure 5:
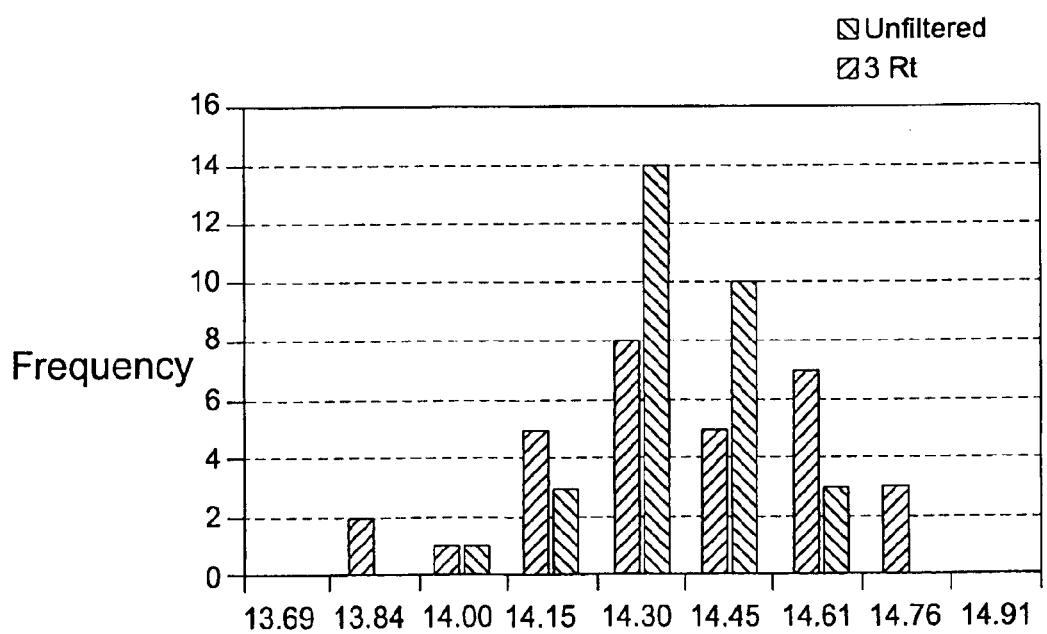
FIG. 5 is a graph depicting the edge position measurements for a series of 31 scans.

The edge sensing capability of the edge sensor 10 at a stand off distance is beneficial when scanning a substrate surface where the edge sensor 10 needs to clear a rivet head. Even though the shape of the curves in FIG. 5 are different for the contact and the stand off modes, the important result is that each scan produces the same edge position 30 as shown by the dotted line. To achieve precise edge sensing, there must a statistically significant difference between the measured count rate before and after the edge. The count rate differential diminishes slowly with standoff distance. For standoff distances greater than 0.394 inches (10 mm), the effectiveness of the edge sensor 10 is determined by the ability to measure a statistically significant count rate differential before and after the edge.

A second test evaluated the precision and repeatability of the edge sensor 10 to locate the edge 28. The edge sensor 10 was mounted on a linear motion control unit with positional accuracy of 0.0004 inches (0.01 mm) and series of scans were made with the edge sensor 10 on an aluminum substrate to determine the statistical spread of the measured edge distance. At a scanning speed of 2.5 inches per min (63.5 mm/min) a typical measurement of the backscatter count rate for a one inch (25 mm) scan is shown by the data points of FIG. 4. The standoff distance from the substrate blind surface 34 was approximately 0.063 inches (1.6 mm). The fluctuation of the data is due to the counting statistics, since the measurement interval for each point is only 0.4 seconds. Data filtering or smoothing techniques were used to reduce the fluctuations. A 3-point smooth of the measured data is shown by the solid curve in the FIG. 4.

A third test evaluated the effectiveness of filtering or smoothing for which a series of thirty one successive scans were taken to assess the precision of the edge measurement with and without filtering applied to the data. FIG. 5 shows the frequency distribution of the measured edge position for the 31 scans at a speed of 2.5 inches per min (63.5 mm/min.) over the edge 28 with the results binned in 0.006 inch intervals (0.15 mm). The mean edge position is 0.563 inches (14.3 mm) for both the filtered and the unfiltered data. This shows excellent agreement with the actual edge distance of 0.563 inches (14.3 mm) as determined with calipers.

Although the means of these distributions are identical, the standard deviations are significantly different. For the unfiltered data, one standard deviation is +/−0.010, for the 3-point filter it is +/−0.005. Hence, the filtering improves the precision by a factor of 2.

For the 3-point filter, the range of measurements extends from 0.551 inches (14.0 mm) to 0.572 inches (14.53 mm). As such, all of the measured edge position are within (?+/−0.112?) inches of the actual edge position which implies that a 0.016 inch (0.4 mm) allowance for offset of the drill beyond the prescribed distance will assure proper edge distance for all drilled holes.

A fourth test evaluated accuracy of the edge sensor 10 at various scan speeds of the edge sensor over a hidden edge of a structure. The results show that for speeds up to 9.843 inches per min (250 mm/min.) the precision of the edge location measurements was maintained within a few thousandths of an inch (a few tenths of a mm).

What is claimed is:

1. An edge sensor for identifying a position of an edge on a substrate, the sensor comprising:
    a. a stainless steel cylinder;
    b. a radiation source contained within the stainless steel cylinder and capable of emitting radiation backscatterable by the substrate;
    c. a scanner attached to the radiation source for detecting a count rate from the radiation backscattered by the substrate;
    d. a position sensor capable of locating a position of the backscattered radiation on the substrate;
    e. a microprocessor in electrical communication with the scanner and position sensor which receives the count rate and the positional data therefrom, then calculates the edge position; and
    f. an indicator which receives and indicates the calculated edge position.

2. The edge sensor of claim 1 wherein the emitted radiation is collimated by a collimator.

3. The edge sensor of claim 1 wherein the radiation source emits radiation at levels of approximately 0.8 microSievert/hr or 0.08 millirem/hr at 12 from the gauge tip for 241 AM, and 0.5 mSv/hr or 0.05 mrem/hr for 57 Co.

4. The edge sensor of claim 1 wherein the scanner is a cesium iodide crystal.

5. The edge sensor of claim 4 wherein the crystal has a thin annular shape.

6. The edge sensor of claim 5 wherein the crystal surrounds the collimator.

7. The edge sensor of claim 1 further comprising a photomultiplier attached to the scanner.

8. An edge sensor for identifying a position of an edge on a substrate, the sensor comprising:
    a. a radiation source capable of emitting radiation backscatterable by the substrate;
    b. a scanner attached to the radiation source for detecting a count rate from the radiation backscattered by the substrate;
    c. a position sensor capable of locating a position of the backscattered radiation on the substrate;
    d. a microprocessor in electrical communication with the scanner and position sensor which receives the count rate and the positional data therefrom, then calculates the edge position;
    e. an indicator which receives and indicates the calculated edge position; and
    f. a charge sensitive amplifier connected to the scanner with a shielded cable.

9. The edge sensor of claim 1 wherein the indicator is a monitor which depicts the edge position as a response function centroid.

10. The edge sensor of claim 1 wherein the indicator is a light emitting diode.

11. An edge sensing CNC machine which machines parts, the machine comprising:
    a) a CNC machine; and
    b) an edge sensor attached to the CNC machine for identifying a position of an edge on a substrate, the edge sensor comprising:
        i) a radiation source capable of emitting radiation backscatterable by the part;
        ii) a scanner attached to the radiation source for detecting a count rate from the radiation backscattered by the part;
        iii) a position sensor capable of locating a position of the backscattered radiation on the part;
        iv) a microprocessor in electrical communication with the scanner and position sensor which receives the count rate and the positional data therefrom, then calculates the edge position.

12. A method of locating an edge under a substrate, the method comprising:
    a. containing backscatterable radiation within a metal container;
    b. emitting backscatterable radiation onto the substrate;
    c. detecting the radiation backscattered from the substrate;
    d. associating a position with the detected radiation;
    e. repeating steps a), b), c) and d) along a line on the substrate wherein the line crosses the edge; and
    f. determining a response function, statistically significant count rate before the edge and a statistically significant count rate after the edge.

13. The method of claim 12 wherein the emitting step emits radiation at least partially penetrable through a thin portion of the substrate.

14. The method of claim 13 wherein the emitting step includes the step of collimating the emitted radiation.

15. The method of claim 14 wherein the collimating step is accomplished with a collimator.

16. The method of claim 15 wherein the detecting step is performed with a scanner.

17. The method of claim 16 wherein the scanner is a cesium iodide crystal.

18. The method of claim 17 wherein the crystal has an annular shape.

19. The method of claim 18 wherein the crystal is about 0.100 inches thick.

20. The method of claim 12 wherein step e is repeated along a plurality of parallel lines to obtain a two dimensional representation of the edge.

21. The method of claim 12 wherein step e is repeated along the line wherein the line length is truncated at both ends of the line.

22. An edge sensor for identifying a position of an edge on a substrate, the sensor comprising:
    a. a metal container;
    b. a radiation source contained within the container and capable of emitting radiation backscatterable by the substrate;
    c. a scanner attached to the radiation source for detecting a count rate from the radiation backscattered by the substrate;

d. a position sensor capable of locating a position of the backscattered radiation on the substrate;

e. a microprocessor in electrical communication with the scanner and position sensor which receives the count rate and the positional data therefrom, then calculates the edge position; and f. an indicator which receives and indicates the calculated edge position.

23. An edge sensing CNC machine which machines parts, the machine comprising:

a) a computer controlled machine; and b) an edge sensor attached to the computer controlled machine for identifying a position of an edge on a substrate, the edge sensor comprising:

i) a radiation source capable of emitting radiation backscatterable by the part;

ii) a scanner attached to the radiation source for detecting a count rate from the radiation backscattered by the part;

iii) a position sensor capable of locating a position of the backscattered radiation on the part;

iv) a microprocessor in electrical communication with the scanner and position sensor which receives the count rate and the positional data therefrom, then calculates the edge position.

24. The edge sensor of claim 8 further comprising a voltage comparator connected to the scanner.

* * * * *